United States Patent
Barry et al.

(10) Patent No.: US 11,795,477 B2
(45) Date of Patent: *Oct. 24, 2023

(54) SINGLE CYCLE REPLICATING ADENOVIRUS VECTORS

(71) Applicant: Mayo Foundation for Medical Education and Research, Rochester, MN (US)

(72) Inventors: Michael A. Barry, Rochester, MN (US); Eric Weaver, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/671,294

(22) Filed: Feb. 14, 2022

(65) Prior Publication Data
US 2022/0170046 A1 Jun. 2, 2022

Related U.S. Application Data

(60) Continuation of application No. 16/863,705, filed on Apr. 30, 2020, now Pat. No. 11,279,953, which is a continuation of application No. 16/570,535, filed on Sep. 13, 2019, now Pat. No. 10,640,786, which is a continuation of application No. 16/153,880, filed on Oct. 8, 2018, now Pat. No. 10,465,206, which is a division of application No. 12/920,775, filed as application No. PCT/US2009/036392 on Mar. 6, 2009, now Pat. No. 10,131,921.

(60) Provisional application No. 61/068,287, filed on Mar. 6, 2008.

(51) Int. Cl.
*A61K 39/12* (2006.01)
*A61K 39/00* (2006.01)
*C12N 15/86* (2006.01)

(52) U.S. Cl.
CPC .............. *C12N 15/86* (2013.01); *A61K 39/12* (2013.01); *A61K 39/00* (2013.01); *A61K 2039/542* (2013.01); *C12N 2710/10343* (2013.01)

(58) Field of Classification Search
None
See application file for complete search history.

(56) References Cited

U.S. PATENT DOCUMENTS

| | | | |
|---|---|---|---|
| 6,569,677 B1 | 5/2003 | Legrand et al. | |
| 10,131,921 B2 | 11/2018 | Barry et al. | |
| 10,640,786 B2 * | 5/2020 | Barry | A61P 37/04 |
| 11,149,286 B1 | 10/2021 | Barry | |
| 11,279,953 B2 | 3/2022 | Barry et al. | |
| 2006/0062764 A1 | 3/2006 | Police et al. | |
| 2017/0137843 A1 | 5/2017 | Mebatsion et al. | |
| 2019/0093127 A1 | 3/2019 | Barry et al. | |
| 2020/0002725 A1 | 1/2020 | Barry et al. | |
| 2020/0255865 A1 | 8/2020 | Barry et al. | |
| 2022/0049271 A1 * | 2/2022 | Barry | A61K 39/12 |

FOREIGN PATENT DOCUMENTS

| | | |
|---|---|---|
| CN | 111088283 | 6/2020 |
| CN | 111529685 | 8/2020 |
| CN | 111560076 | 8/2020 |
| WO | WO 2009/111738 | 9/2009 |

OTHER PUBLICATIONS

Aboudola et al., "Clostridium difficile vaccine and serum immunoglobulin G antibody response to toxin A," Infec. Immunity, Mar. 2003, 71(3):1608-1610.
Aktories et al., "Clostridium difficile toxin biology," Annu. Rev. Microbiology, Sep. 2017, 71:281-307.
Anguiano-Zarate et al., "A replicating single-cycle adenovirus vaccine against Ebola virus," J. Infect. Diseases, Nov. 2018, 218(12):1883-1889.
Anosova et al., "Systemic antibody responses induced by a two-component Clostridium difficile toxoid vaccine protect against C. difficile-associated disease in hamsters," J. Med. Microbiology, Sep. 2013, 62(9):1394-1404.
Authorized Officer Philippe Becamel, International Preliminary Report on Patentability re PCT/US2009/036392, dated Sep. 7, 2010, 4 pages.
Authorized Officer Weon Hye Shin, Written Opinion of the International Searching Authority re PCT/US2009/036392, completed Jul. 30, 2009, 3 pages.
Babcock et al., "Human monoclonal antibodies directed against toxins A and B prevent Clostridium difficile-induced mortality in hamsters," Infec. Immunity, Nov. 2006, 74(11):6339-6347.
Baliban et al., "An optimized, synthetic DNA vaccine encoding the toxin A and toxin B receptor binding domains of Clostridium difficile induces protective antibody responses in vivo," Infec. Immunity, Oct. 2014, 82(10):4080-4091.
Barefoot et al., "Comparison of multiple vaccine vectors in a single heterologous prime-boost trial," Vaccine, Nov. 2008, 26(48):6108-6118.
Barouch et al., "Control of viremia and prevention of clinical AIDS in rhesus monkeys by cytokine-augmented DNA vaccination," Science, 2000, 290:486-492.
Barry and Johnston, "Biological features of genetic immunization," Vaccine, 1997, 15:788-791.
Barry et al., "Expression Library Immunization To Discover And Improve Vaccine Antigens," Immunological Reviews, 2004, 199:68-83.

(Continued)

*Primary Examiner* — Benjamin P Blumel
(74) *Attorney, Agent, or Firm* — Fish & Richardson P.C.

(57) ABSTRACT

This document relates to adenovirus vectors and methods and materials related to using adenovirus vectors. For example, viruses, nucleic acid molecules encoding viruses, cell lines containing viral vectors, and methods for using viruses to deliver nucleic acid to cells in vitro or in vivo are provided. Methods and materials for using adenovirus vectors to induce immune responses and to treat cancer also are provided.

6 Claims, 6 Drawing Sheets
Specification includes a Sequence Listing.

(56) References Cited

OTHER PUBLICATIONS

Barry et al., "Production of monoclonal antibodies by genetic immunization," Biotechniques, 1994, 16:616-619.
Barry et al., "Protection against mycoplasma infection using expression library immunization: A general approach to vaccine development," Nature, 1995, 377:632-635.
Barry et al., "Role of endogenous endonucleases and tissue site in transfection and CpG-mediated immune activation after naked DNA injection," Human Gene Therapy, 1999, 10:2461-2480.
Basnight et al., "Characterization of four new adenovirus serotypes isolated from chimpanzee tissue explants," Am J Epidemiol., 1971, 94:166-171.
Benson et al., "Recombinant vaccine-induced protection against the highly pathogenic simian immunodeficiency virus SIVmac251: dependence on route of challenge exposure," J. Virol., 1998, 72:4170-4182.
Bergelson et al., "Isolation of a common receptor for Coxsackie B viruses and adenoviruses 2 and 5," Science, 1997, 275:1320-1323.
Brayden, "Oral vaccination in man using antigens in particles: current status," Eur J Pharm Sci., 14:183-189.
Buge et al., "Factors Associated with Slow Disease Progression in Macaques Immunized with an Adenovirus-Simian Immunodeficiency Virus (SIV) Envelope Priming-gp120 Boosting Regimen and Challenged Vaginally with SIVmac2 51," J Virol., 1999, 73:7430-7440.
Buge et al., "An adenovirus-simian immunodeficiency virus env vaccine elicits humoral, cellular, and mucosal immune responses in rhesus macaques and decreases viral burden following vaginal challenge," J. Virol., 1997, 71:8531-8541.
Campos and Barry, "Comparison of adenovirus fiber, protein IX, and hexon capsomeres as scaffolds for vector purification and cell targeting," Virology, 2006, 349:453-462.
Campos and Barry, "Current advances and future challenges in Adenoviral vector biology and targeting," Curr Gene Ther., 2007, 7:189-204.
Campos and Barry, "Rapid construction of capsid-modified adenoviral vectors through bacteriophage lambda Red recombination," Hum Gene Ther., 2004, 15:1125-1130.
Carter et al., "The role of toxin A and toxin B in Clostridium difficile-associated disease: Past and present perspectives," Gut Microbes, Jan. 2010, 1(1):58-64.
Casimiro et al., "Comparative immunogenicity in rhesus monkeys of DNA plasmid, recombinant vaccinia virus, and replication-defective adenoviral vectors expressing a human immunodeficiency virus type 1 gag gene," J. Virol., 2003, 77:6305-6313.
Casimiro et al., "Vaccine-induced immunity in baboons by using DNA and replicationincompetent adenovirus type 5 vectors expressing a human immunodeficiency virus type 1 gag gene," J Virol., 2003, 77:7663-7668.
Caulfield et al., "Sustained Peptide-Specific Gamma Interferon T-Cell Response in Rhesus Macaques Immunized with Human Immunodeficiency Virus gag DNA Vaccines," J Virol., 2002, 76:10038-10043.
Chai et al., "Management of primary and recurrent Clostridium difficile infection: an update," Antibiotics, Sep. 2018, 7(3):54, 8 pages.
Cheng et al., "PEGylated adenoviruses for gene delivery to the intestinal epithelium by the oral route," Pharm Res., 2003, 20:1444-1451.
Couch et al., "Immunization with types 4 and 7 adenovirus by selective infection of the intestinal tract," Am Rev Respir Dis., 1963, 88:SUPPL 394-403.
Crosby et al., "Amplified and persistent immune responses generated by single-cycle replicating adenovirus vaccines," J. Virology, Jan. 2015, 89(1):669-675.
Crosby et al., "IIIa deleted adenovirus as a single-cycle genome replicating vector," Virol. Journal, Aug. 2014, 462:158-165.

Crosby et al., "Replicating single-cycle adenovirus vectors generate amplified influenza vaccine responses," J. Virology, Jan. 2017, 91(2):e00720-16, 12 pages.
Crosby et al., "Transgene expression and host cell responses to replication-defective, singlecycle, and replication-competent adenovirus vectors," Genes, Feb. 2017, 8(2):79, 14 pages.
Crotty et al., "Protection against simian immunodeficiency virus vaginal challenge by using Sabin poliovirus vectors," J Virol., 2001, 75:7435-7452.
Croyle et al., "Nasal delivery of an adenovirus-based vaccine bypasses pre-existing immunity to the vaccine carrier and improves the immune response in mice," PLoS One, Oct. 2008, 3(10):e3548, 9 pages.
Croyle et al., "'Stealth' adenoviruses blunt cell-mediated and humoral immune responses against the virus and allow for significant gene expression upon readministration in the lung," J Virol., 2001, 75:4792-4801.
Croyle et al., "Development of a rapid method for the PEGylation of adenoviruses with enhanced transduction and improved stability under harsh storage conditions," Hum Gene Ther., 2000, 11:1713-1722.
Croyle et al., "Development of formulations that enhance physical stability of viral vectors for gene therapy," Gene Ther., 2001, 8:1281-1290.
Croyle et al., "PEGylation of E1-deleted adenovirus vectors allows significant gene expression on readministration to liver," Hum Gene Ther., 2002, 13:1887-1900.
Dale et al., "Chimeric human papilloma virus-simian/human immunodeficiency virus virus-like-particle vaccines: immunogenicity and protective efficacy in macaques," Virology, 2002, 301:176-187.
D'ambrosio et al., "Neutralizing antibodies against 33 human adenoviruses in normal children in Rome," Epidemiol. Infection, Aug. 1982, 89(1):155-161.
Daniel et al., "Protective effects of a live attenuated SIV vaccine with a deletion of the nef gene," Science, 1992, 258:1938-1941.
Davis and Matyjaszewski, "Atom transfer radical polymerization of tert-butyl acrylate and preparation of block copolymers," Macromolecules, 2000, 33:4039.
Demberg et al., "A replication-competent adenovirus-human immunodeficiency virus (Ad-HIV) tat and Ad-HIV env priming/Tat and envelope protein boosting regimen elicits enhanced protective efficacy against simian/human immunodeficiency virus SHIV89.6P challenge in rhesus macaques," J Virol., 2007, 81:3414-3427.
DePestel et al., "Epidemiology of Clostridium difficile infection," J. Pharm. Practice, Oct. 2013, 26(5):464-475.
Dicks et al., "A Novel Chimpanzee Adenovirus Vector with Low Human Seroprevalence: Improved Systems for Vector Derivation and Comparative Immunogenicity," PLoS One, Jul. 13, 2012, 7(7):e403 85, 12 pages.
Donald et al., "A novel approach to generate a recombinant toxoid vaccine against Clostridium difficile," Microbiology, Jul. 2013, 159(7):1254-1266.
Duncan et al., "Infection of mouse liver by human adenovirus type 5," J Gen Virol., 1978, 40:45-61.
Duraiswamy et al., "Induction of Therapeutic T-Cell Responses to Subdominant Tumor-associated Viral Oncogene after Immunization with Replication-incompetent Polyepitope Adenovirus Vaccine," Cancer Research, 2004, 64:1483-1489.
Fausther-Bovendo et al., "Pre-existing immunity against Ad vectors: humoral, cellular, and innate response, what's important?" Hum. Vaccin. Immunotherapeutics, Oct. 2014, 10(10):2875-2884.
Fields et al., "Role of vector in activation of T cell subsets in immune responses against the secreted transgene product factor IX," Molecular Therapy, 2000, 1:225-235.
Fischinger et al., "Sex differences in vaccine-induced humoral immunity," Semin. Immunopathology, Mar. 2019, 41(2):239-249.
Fisher et al., "Polymer-coated adenovirus permits efficient retargeting and evades neutralising antibodies," Gene Ther., 2001, 8:341-348.
Frey et al., "A statistically defined endpoint titer determination method for immunoassays," J. Immunol. Methods, Dec. 1998, 221(1-2):35-41.

(56) References Cited

OTHER PUBLICATIONS

Frey et al., "Localization of two epitopes recognized by monoclonal antibody PCG-4 on Clostridium difficile toxin A," Infect. Immunity, Jun. 1992, 60(6):2488-2492.
Gardiner et al., "A DNA vaccine targeting the receptor-binding domain of Clostridium difficile toxin A," Vaccine, Jun. 2009, 27(27):3598-3604.
GenBank Accession No. AA024897, gi No. 1489803, dated Jan. 1, 2011, 2 pages.
GenBank Accession No. AAA03229.1, "MAGE-1 [*Homo sapiens*]," dated Jun. 23, 2010, 1 page.
GenBank Accession No. AAD33253.1, "E7 [Human papillomavirus type 16]," dated Jul. 26, 2016, 1 page.
GenBank Accession No. AAD56719.1, "allergen [Arachis hypogaea]," dated May 10, 2010, 1 page.
GenBank Accession No. AB353125, dated Mar. 5, 2008, 13 pages.
GenBank Accession No. AF030154, dated Oct. 20, 2000, 13 pages.
GenBank Accession No. AF268967, dated Jul. 31, 2000, 2 pages.
GenBank Accession No. AY772062.1, "SARS coronavirus WH20, complete genome," dated Mar. 25, 2009, 10 pages.
GenBank Accession No. BC109215, dated Aug. 7, 2008, 2 pages.
GenBank Accession No. CAA30155, gi No. 4582, dated Jun. 12, 2006, 2 pages.
GenBank Accession No. CEQ32409.1, "LMP-1 [Human gammaherpesvirus 4]," dated Sep. 24, 2015, 1 page.
GenBank Accession No. D55656S08, gi No. 951475, dated Dec. 26, 2002, 3 pages.
GenBank Accession No. DQ227321, dated Jun. 1, 2007, 6 pages.
GenBank Accession No. DQ437592, dated Aug. 19, 2006, 79 pages.
GenBank Accession No. EU497921, dated Dec. 22, 2008, 2 pages.
GenBank Accession No. K02718, dated Mar. 18, 1994, 4 pages.
GenBank Accession No. L12723, dated Sep. 8, 1993, 2 pages.
GenBank Accession No. M73260, dated Apr. 8, 1996, 10 pages.
GenBank Accession No. M92650, dated Nov. 7, 1994, 2 pages.
GenBank Accession No. MN938384, "Wuhan seafood market pneumonia virus isolate 2019-nCoV_HKU-SZ-002a_2020, complete genome," dated Jan. 24, 2020, 10 pages.
GenBank Accession No. NC_001798, dated Apr. 23, 2010, 65 pages.
GenBank Accession No. NC_001802, dated Dec. 8, 2008, 8 pages.
GenBank Accession No. NC_004102, dated Jun. 18, 2009, 6 pages.
GenBank Accession No. NM_000282, dated Mar. 31, 2012, 5 pages.
GenBank Accession No. NM_000453, dated Apr. 1, 2012, 6 pages.
GenBank Accession No. NM_004988, dated Apr. 22, 2012, 4 pages.
GenBank Accession No. NP_001003190.1, "major allergen Can f 1 precursor [Canis lupus familiaris]," dated Jul. 23, 2019.
GenBank Accession No. NP_001191706.1, "Fel d 7 allergen precursor [Felis catus]," dated Mar. 1, 2018, 1 page.
GenBank Accession No. NP_001363134.1, "profilin [Arachis hypogaea]," dated Nov. 11, 2019, 2 pages.
GenBank Accession No. NP_001363136.1, "allergen Ara h 1, clone P17 precursor [Arachis hypogaea]," dated Nov. 11, 2019, 2 pages.
GenBank Accession No. NP_001363139.1, "allergen Ara h 1, clone P41B precursor [Arachis hypogaea]," dated Nov. 12, 2019, 2 pages.
GenBank Accession No. P10414.2, "RecName: Full=Pollen allergen Amb t 5; AltName: Full=Allergen Amb t V; AltName: Full=Allergen Ra5G; AltName: Allergen=Amb 15; Flags: Precursor," dated May 23, 2018, 2 pages.
GenBank Accession No. P15494.2, "RecName: Full=Major pollen allergen Bet v 1-A; AltName: Full=Allergen Bet v I-A; AltName: Allergen-Bet v 1-A," dated Jul. 3, 2019, 4 pages.
GenBank Accession No. P27762.1, "RecName: Full=Pectate lyase 4; AltName: Full=Antigen Amb a II; AltName: Full=Antigen K; Short=AgK; AltName: Full=Pollen allergen Amb a 2; AltName: Allergen=Amb a 2; Flags: Precursor," dated Dec. 5, 2018, 2 pages.
GenBank Accession No. P43176.2, "RecName: Full=Major pollen allergen Bet v 1-C; AltName: Full=Allergen Bet v I-C; AltName: Allergen-Bet v 1-C," dated Jul. 3, 2019, 2 pages.
GenBank Accession No. Q02496.2, "RecName: Full=Mucin-1; Short-MUC-1; AltName: Full=Episialin; AltName: CD_antigen=CD227; Contains: RecName: Full=Mucin-1 subunit alpha; Short-MUC1-NT; Short-MUC1-alpha; Contains: RecName: Full-Mucin-1 subunit beta; Short=MUC1-beta; AltName: Full=MUC1-CT; Flags: Precursor," dated Feb. 13, 2019, 6 pages.
GenBank Accession No. QAR15051.1, "EBNA-1 [Human gammaherpesvirus 4]," dated Jan. 18, 2019, 1 page.
GenBank Accession No. X02777, gi No. 3308, dated Oct. 23, 2008, 2 pages.
GenBank Accession No. XI5980, gi No. 7157, dated Mar. 31, 1995, 2 pages.
GenBank Accession No. XI7016, Apr. 18, 2005, 2 pages.
GenBank Accession No. X17329, gi No. 1756, Oct. 21, 2008, 2 pages.
GenBank Accession No. X51613, gi No. 5095, dated Nov. 14, 2006, 2 pages.
GenBank Accession No. X65470, gi No. 4100, dated Apr. 18, 2005, 2 pages.
GenBank Accession No. XP_001657779.1, "37 kDa salivary gland allergen Aed a 2 [Aedes aegypti]," dated Jul. 20, 2017, 1 page.
GenBank Accession No. XP_002754883.1, "folate receptor alpha [Callithrix jacchus]," dated Aug. 31, 2016, 1 page.
GenBank Accession No. XP_030099003.1, "major allergen I polypeptide chain 1 [Mus musculus]," dated Aug. 8, 2019, 1 page.
GenBank Accession No. YP_401631.1, "membrane protein LMP-2A [Human gammaherpesvirus 4]," dated Aug. 13, 2018, 2 pages.
GenBank Accession No. YP_401632.1, "membrane protein LMP-2B [Human gammaherpesvirus 4]," dated Aug. 13, 2018, 2 pages.
GenBank Accession No. Z14860, gi No. 6528, dated Jan. 25, 2011, 2 pages.
GenBank Accession No. Z17325, dated Dec. 3, 1992, 1 page.
Gomez-Roman et al., "An adenovirus-based HIV subtype B prime/boost vaccine regimen elicits antibodies mediating broad antibody-dependent cellular cytotoxicity against non-subtype B HIV strains," J Acquir Immune Defic Syndr, 2006, 43:270-277.
Gomez-Roman et al., "Oral delivery of replication-competent adenovirus vectors is well tolerated by SIV- and SHIV-infected rhesus macaques," Vaccine, 2006, 24:5064-5072.
Gould-Fogerite et al., "Targeting immune response induction with cochleate and liposome-based vaccines," Adv Drug Deliv Rev., 1998, 32:273-287.
Graham et al., "Evaluation of the immunogenicity of prime-boost vaccination with the replication-deficient viral vectored COVID-19 vaccine candidate ChAdOxl nCoV-19", NPJ Vaccine, 2020, 69:1-6.
Greco et al., "Carbohydrate recognition by Clostridium difficile toxin A," Nat. Struct. Mol. Biology, May 2006, 13(5):460-461.
Greenwald et al., "Drug delivery systems employing 1,4- or 1,6-elimination: poly(ethylene glycol) prodrugs of amine-containing compounds," J Med Chem., 1999, 42:3657-3667.
Henderson et al., "A review of the safety and efficacy of vaccines as prophylaxis for Clostridium difficile infections," Vaccines, Sep. 2017, 5(3):25, 9 pages.
Hofherr et al., "Polyethylene Glycol Modification of Adenovirus Reduces Platelet Activation, Endothelial Cell Activation, and Thrombocytopenia," Human Gene Therapy, 2007, 18:837-848.
Howell et al., "Deoxyribonuclease II is a lysosomal barrier to transfection," Mol Ther., 2003, 8:957-963.
Huang et al., "Adenovirus interaction with distinct integrins mediates separate events in cell entry and gene delivery to hematopoietic cells," J. Virol., 1996, 70:4502-4508.
Hutton et al., "Small animal models for the study of Clostridium difficile disease pathogenesis," FEMS Microbiol. Letters, Mar. 2014, 352(2):140-149.
Igarashi et al., "Protection of monkeys vaccinated with vpr- and/or nef-defective simian immunodeficiency virus strain mac/human immunodeficiency virus type 1 chimeric viruses: a potential candidate live-attenuated human AIDS vaccine," Journal of General Virology, 1997, 78:985-989.
Ji, "Lysis of cultured cells for immunoprecipitation," Cold Spring Harb. Protocols, Aug. 2010, 2010(8):pdb-rot5466, 5 pages.

(56) References Cited

OTHER PUBLICATIONS

Jin et al., "Immunization with adenoviral vectors carrying recombinant IL-12 and E7 enhanced the antitumor immunity to human papillomavirus 16-associated tumor," Gynecologic Oncology, 2005, 97:559-567.
Johnston and Barry, "Genetic to genomic vaccination," Vaccine, 1997, 15:808-809.
Kaneko et al., "Oral DNA vaccination promotes mucosal and systemic immune responses to HTV envelope glycoprotein," Virology, 2000, 267:8-16.
Kaplan et al., "Induction of Antitumor Immunity with Dendritic Cells Transduced with Adenovirus Vector-Encoding Endogenous Tumor-Associated Antigens," Journal of Immunology, 1999, 163:699-707.
Kelly et al., "Clostridium difficile—more difficult than ever," N. Engl. J. Medicine, Oct. 2008, 359(18):1932-1940.
Kim et al., "Immunization of adult hamsters against Clostridium difficile-associated ileocecitis and transfer of protection to infant hamsters," Infect. Immunity, Dec. 1987, 55(12):2984-2992.
Kink et al., "Antibodies to recombinant Clostridium difficile toxins A and B are an effective treatment and prevent relapse of C. difficile-associated disease in a hamster model of infection," Infect. Immunity, May 1998, 66(5):2018-2025.
Kuehne et al., "Importance of toxin A, toxin B, and CDT in virulence of an epidemic Clostridium difficile strain," J. Infect. Diseases, Jan. 2014, 209(1):83-86.
Kuehne et al., "The role of toxin A and toxin B in Clostridium difficile infection," Nature, Oct. 2010, 467(7316):711-713.
Kuipers et al., "Clostridium difficile infection," The Lancet, May 2008, 371(9623):1486-1488.
Kuroda and DeGrado, "Amphiphilic polymethacrylate derivatives as antimicrobial agents," J Am Chem Soc., 2005, 127:4128-4129.
Kyne et al., "Asymptomatic carriage of Clostridium difficile and serum levels of IgG antibody against toxin A," N. Engl. J. Medicine, Feb. 2000, 342(6):390-397.
Lam et al., "Cost-effectiveness of three different strategies for the treatment of first recurrent Clostridium difficile infection diagnosed in a community setting," Infect. Control Hosp. Epidemiology, Aug. 2018, 39(8):924-930.
Leav et al., "Serum anti-toxin B antibody correlates with protection from recurrent Clostridium difficile infection (CDI)," Vaccine, Jan. 2010, 28(4):965-969.
Lee et al., "Bezlotoxumab (Zinplava) for clostridium difficile infection: the first monoclonal antibody approved to prevent the recurrence of a bacterial infection," Pharm. Therapeutics, Dec. 2017, 42(12):735-738.
Leffler et al., "Clostridium difficile infection," N. Engl. J. Medicine, Apr. 2015, 372(16):1539-1548.
Lehner and Anton, "Mucosal immunity and vaccination against HIV," Aids 16 Suppl., 2002, 4:S125-132.
Lessa et al., "Burden of Clostridium difficile infection in the United States," N. Engl. J. Medicine, Feb. 2015, 372(9):825-834.
Lowy et al., "Treatment with monoclonal antibodies against Clostridium difficile toxins," N. Engl. J. Medicine, Jan. 2010, 362(3):197-205.
Lu et al., "Use of DNAs expressing HIV-1 env and noninfectious HIV-1 particles to raise antibody responses in mice," Virology, 1995, 209:147-154.
Lubeck et al., "Long-term protection of chimpanzees against high-dose HTV-1 challenge induced by immunization," Nat Med., 1997, 3:651-658.
Lyerly et al., "Characterization of toxins A and B of Clostridium difficile with monoclonal antibodies," Infect. Immunity, Oct. 1986, 54(1):70-76.
Lyerly et al., "Clostridium difficile: its disease and toxins," Clin. Microbiol. Reviews, Jan. 1988, 1(1):1-18.
Ma et al., "Increasing incidence of multiply recurrent Clostridium difficile infection in the United States: a cohort study," Ann. Intern. Medicine, Aug. 2017, 167(3):152-158.
Malkevitch et al., "A replication competent adenovirus 5 host range mutant-simian immunodeficiency virus (SiV) recombinant priming/subunit protein boosting vaccine regimen induces broad, persistent SIV-specific cellular immunity to dominant and subdominant epitopes in Mamu-A*01 rhesus macaques," J Immunol., 2003, 170:4281-4289.
Malkevitch et al., "Durable protection of rhesus macaques immunized with a replicating adenovirus-SIV multigene prime/protein boost vaccine regimen against a second SIVmac251 rectal challenge: role of SIV-specific CD8+ T cell responses," Virology, 2006, 353:83-98.
Matchett et al., "Divergent HIV-1-directed immune responses generated by systemic and mucosal immunization with replicating single-cycle adenoviruses in rhesus macaques," J. Virology, May 2019, 93(10):e02016-18, 18 pages.
Matchett et al., "Genetic Adjuvants in Replicating Single-Cycle Adenovirus Vectors Amplify Systemic and Mucosal Immune Responses against HIV-1 Envelope," Vaccines, Mar. 2020, 8(1):64, 13 pages.
Matthews, "Adenovirus protein V induces redistribution of nucleolin and B23 from nucleolus to cytoplasm," J Virol., 2001, 75:1031-1038.
Matyjaszewski and Xia, "Atom transfer radical polymerization," Chem Rev., 2001, 101:2921-2990.
McDonald et al., "Clinical practice guidelines for Clostridium difficile infection in adults and children: 2017 update by the Infectious Diseases Society of America (IDSA) and Society for Healthcare Epidemiology of America (SHEA)," Clin. Infect. Diseases, Mar. 2018, 66(7):e1-48.
McFarland et al., "Breaking the cycle: treatment strategies for 163 cases of recurrent Clostridium difficile disease," Am. J. Gastroenterology, Jul. 2002, 97(7):1769-1775.
Mennechet et al., "A review of 65 years of human adenovirus seroprevalence," Expert Rev. Vaccines, Jun. 2019, 18(6):597-613.
Mercier et al., "A chimeric adenovirus vector encoding reovirus attachment protein sigma1 targets cells expressing junctional adhesion molecule 1," Proc Natl Acad Sci USA, 2004, 101:6188-6193.
Mercier et al., "Oral immunization of rhesus macaques with adenoviral HIV vaccines using enteric-coated capsules," Vaccine, 2007, 25:8687-8701.
Mittall et al., "Immunization with DNA, adenovirus, or both in biodegradable alginate microspheres: effect of route of inoculation on immune response," Vaccine, 2000, 19:253-263.
Mok and Barry, "Evaluation of Polyethylene Glycol (PEG)-modification of First Generation and Helper-Dependent Adenoviral Vectors to Reduce Innate Immune Responses," Molecular Therapy, 2005, 11:66-79.
Mossman et al., "Protection against lethal simian immunodeficiency virus SIVsmmPBjM disease by a recombinant Semliki Forest virus gp160 vaccine and by a gp120 subunit vaccine," J Virol, 1996, 70:1953-1960.
Mullard, "FDA approves antitoxin antibody," Nat. Rev. Drug Discovery, Nov. 2016, 15:811.
Munoz et al., "Disseminated adenovirus disease in immunocompromised and immunocompetent children," Clin. Infect. Diseases, Nov. 1998, 27(5):1194-1200.
Natuk et al., "Adenovirus-human immunodeficiency virus (HIV)envelope recombinant vaccines elicit high-titered HIV-neutralizing antibodies in the dog model," Proc Nat Acad Sci USA, 1992, 89:7777-7781.
Nehete et al., "A synthetic peptide from the first conserved region in the envelope protein gp160 is a strong T-cell epitope in HIV-infected chimpanzees and humans," Viral Immunol, 1998, 11:147-158.
Nehete et al., "Presence of HLA-C-restricted cytotoxic T-lymphocyte responses in long- term nonprogressors infected with human immunodeficiency virus," Viral Immunol, 1998, 11:119-129.
Nehete et al., "Protection against chronic infection and AIDS by an HIV envelope peptide-cocktail vaccine in a pathogenic SHIV-rhesus model," Vaccine, 2001, 20:813-825.
Nehete et al., "Protection by dendritic cells-based HIV synthetic peptide cocktail vaccine: preclinical studies in the SHIV-rhesus model," Vaccine, 2005, 23:2154-2159.
Nicklin et al., "The influence of adenovirus fiber structure and function on vector development for gene therapy," Mol Ther., 2005, 12:384-393.

(56) References Cited

OTHER PUBLICATIONS

Nyberg-Hoffinan et al., "Sensitivity and reproducibility in adenoviral infectious titer determination," Nat. Medicine, Jul. 1997, 3(7):808-811.
Ohtani et al., "Quantitative analysis of p53-targeted gene expression and visualization of p53 transcriptional activity following intratumoral administration of adenoviral p53 in vivo," Molecular Cancer Therapeutics, 2004, 3(1):93-100.
Oren et al., "Clostridium difficile and Clostridioides difficile: two validly published and correct names," Anaerobe, Aug. 2018, 52:125-126.
O'Riordan et al., "PEGylation of adenovirus with retention of infectivity and protection from neutralizing antibody in vitro and in vivo," Hum Gene Ther, 1999, 10:1349-1358.
Orson et al., "Genetic immunization with lung-targeting macroaggregated polyethyleneimine-albumin conjugates elicits combined systemic and mucosal immune responses," J Immunol., 2000, 164:6313-6321.
Oualikene et al., "Protease-deleted adenovirus vectors and complementing cell lines: potential applications of single-round replication mutants for vaccination and gene therapy," Hum Gene Ther, 2000, 11:1341-1353.
Ourmanov et al., "Comparative efficacy of recombinant modified vaccinia virus Ankara expressing simian immunodeficiency virus (SIV) Gag-Pol and/or Env in macaques challenged with pathogenic SIV," J Virol, 2000, 74:2740-2751.
Parks et al., "Use of helper-dependent adenoviral vectors of alternative serotypes permits repeat vector administration," Gene Ther, 1999, 6:1565-1573.
Parr et al., "Immunity to vaginal infection by herpes simplex virus type 2 in adult mice: characterization of the immunoglobulins in vaginal mucus," J Reprod Immunol, 1998, 38:15-30.
Parrott et al., "Metabolically Biotinylated Adenovirus for Cell-targeting, Ligand Screening, and Vector Purification," Molecular Therapy, 2003, 8:689-702.
Patterson e al., "Protection against mucosal simian immunodeficiency virus SiV(mac251) challenge by using replicating adenovirus-SIV multigene vaccine priming and subunit boosting," J Virol., 2004, 78:2212-2221.
Péchiné et al., "Emerging monoclonal antibodies against Clostridium difficile infection," Expert Opin. Biol. Therapy, Apr. 2017, 17(4):415-427.
Peng et al., "Replicating rather than nonreplicating adenovirus-human immunodeficiency virus recombinant vaccines are better at eliciting potent cellular immunity and priming high-titer antibodies," J Virol., 2005, 79:10200-10209.
Pinczewski et al., "Enhanced immunity and protective efficacy against SIVmac251 intrarectal challenge following ad-SIV priming by multiple mucosal routes and gp120 boosting in MPL-SE," Viral Immunol., 2005, 18:236-243.
Qiu et al., "Novel Clostridium difficile anti-toxin (TcdA and TcdB) humanized monoclonal antibodies demonstrate in vitro neutralization across a broad spectrum of clinical strains and in vivo potency in a hamster spore challenge model," PLoS One, Jun. 2016, 11(6):e0157970, 21 pages.
Rees et al., "Adaptive immune response to Clostridium difficile infection: a perspective for prevention and therapy," Eur. J. Immunology, Mar. 2018, 48(3):398-406.
Richardson et al., "Airway delivery of an adenovirus-based Ebola virus vaccine bypasses existing immunity to homologous adenovirus in nonhuman primates," J. Virology, Apr. 2013, 87(7):3668-3677.
Robert-Guroff et al., "Vaccine protection against a heterologous, non-syncytium-inducing, primary human immunodeficiency virus," J. Virol., 1998, 72:10275-10280.
Rupnik et al., "An update on Clostridium difficile toxinotyping," J. Clin. Microbiology, Jan. 2016, 54(1):13-18.
Sakuma et al., "Biorecognizable HPMA copolymer-drug conjugates for colon-specific delivery of 9-aminocamptothecin," J Control Release, 2001, 75:365-379.
Sauerborn et al., "The C-terminal ligand-binding domain of Clostridium difficile toxin A (TcdA) abrogates TcdA-specific binding to cells and prevents mouse lethality," FEMS Microbiol. Letters, Oct. 1997, 55(1):45-54.
Seregin et al., "Adenovirus-based vaccination against Clostridium difficile toxin A allows for rapid humoral immunity and complete protection from toxin A lethal challenge in mice," Vaccine, Feb. 2012, 30(8):1492-1501.
Shashkova et al., "Targeting Interferon-I Increases Antitumor Efficacy and Reduces Hepatotoxicity of EIA-mutated Spread-enhanced Oncolytic Adenovirus," Mol. Ther., 2007, 15:598-607.
Sheldon et al., "A phase 1, placebo-controlled, randomized study of the safety, tolerability, and immunogenicity of a Clostridium difficile vaccine administered with or without aluminum hydroxide in healthy adults," Vaccine, Apr. 2016, 34(18):2082-2091.
Shields et al., "Recurrent Clostridium difficile infection: from colonization to cure," Anaerobe, Aug. 2015, 34:59-73.
Shiver et al., "Replication-incompetent adenoviral vaccine vector elicits effective anti-immunodeficiency-virus immunity," Nature, 2002, 415:331-335.
Shiver, "A non-replicating adenoviral vector as a potential HIV vaccine," Res Initiat Treat Action., 2003, 8:14-16.
Simecka, "Mucosal immunity of the gastrointestinal tract and oral tolerance," Adv Drug Deliv Rev., 1998, 34:235-259.
Singh and Barry, "Repertoire and immunofocusing of CD8 T cell responses generated by HIV-1 gag-pol and expression library immunization vaccines," Journal of Immunology, 2004, 173:4387-4393.
Singh et al., "Generation of genome-wide CD8 T cell responses in HLA-A*0201 transgenic mice by an HIV-1 ubiquitin expression library immunization vaccine," J Immunol., 2002, 168:379-391.
Sorg et al., "Inhibiting the initiation of Clostridium difficile spore germination using analogs of chenodeoxycholic acid, a bile acid," J. Bacteriology, Oct. 2010, 192(19):4983-4990.
Spencer et al., "Vaccination against Clostridium difficile using toxin fragments: Observations and analysis in animal models," Gut Microbes, Mar. 2014, 5(2):225-232.
Surawicz et al., "Guidelines for Diagnosis, Treatment, and Prevention of Clostridium difficile Infections," Am. J. Gastroenterology, Apr. 2013, 108(4):478-498.
Thomas et al., "Use of the Syrian hamster as an animal model for oncolytic adenovirus vectors," Methods Viol Med., 2007, 130:169-183.
Top et al., "Immunization with live types 7 and 4 adenovirus vaccines. II. Antibody response and protective effect against acute respiratory disease due to adenovirus type 7," J Infect Dis., 1971, 124:155-160.
Tostanoski et al., "Ad26 vaccine protects against SARS-CoV-2 severe clinical disease in hamsters," Nat. Medicine, Sep. 3, 2020, 26(11):1694-1700.
Usala et al., "IgG and IgA content of vaginal fluid during the menstrual cycle," J Reprod Med., 1989, 34:292-294.
Vancikova, "Mucosal immunity-basic principles, ontogeny, cystic fibrosis and mucosal vaccination," Curr Drug Targets Immune Endocr Metabol Disord., 2002, 2:83-95.
Vogels et al., "Replication-deficient human adenovirus type 35 vectors for gene transfer and vaccination: efficient human cell infection and bypass of preexisting adenovirus immunity," J. Virology, Aug. 2003, 77(15):8263-71.
Vogels et al., "Replication-deficient human adenovirus type 35 vectors for gene transfer and vaccination: efficient human cell infection and bypass of preexisting adenovirus immunity," J Virol., 2003, 77:8263-8271.
Wagner et al., "Safety and immunogenicity of recombinant human immunodeficiency virus-like particles in rodents and rhesus macaques," Intervirology, 1996, 39:93-103.
Wang et al., "Gene inoculation generates immune responses against human immunodeficiency virus type 1," Proceedings of the National Academy of Sciences USA, 1993, 90:4156-4160.
Wang, "Induction of humoral and cellular immune responses to the human immunodeficiency type 1 virus in nonhuman primates by in vivo DNA inoculation," Virology, 1995, 211:102-112.

(56) References Cited

OTHER PUBLICATIONS

Weaver et al., "Comparison of systemic and mucosal immunization with helper-dependent adenoviruses for vaccination against mucosal challenge with SHIV," PLoS one, Jul. 2013, 8(7):e67574, 12 pages.

Wickham et al., "Integrins αvβ3 and αvβ5 promote adenovirus internalization but not virus attachment," Cell, 1993, 73:309-319.

Wilcox et al., "Bezlotoxumab for prevention of recurrent Clostridium difficile infection," N. Engl. J. Medicine, Jan. 2017, 376(4):305-317.

Wu and Barry, "Fusion protein vectors to increase protein production and evaluate the immunogenicity of genetic vaccines," Molecular Therapy, 2000, 2:288-297.

Wu and Nemerow. "Virus yoga: the role of flexibility in virus host cell recognition," Trends Microbiol., 2004, 12:162-169.

Xiang et al., "Oral vaccination of mice with adenoviral vectors is not impaired by preexisting immunity to the vaccine carrier," J Virol., 2003, 77:10780-10789.

Xie et al., "Development and optimization of a novel assay to measure neutralizing antibodies against Clostridium difficile toxins," Clin. Vaccine Immunology, Apr. 2013, 20(4):517-25.

Yamshchikov et al., "Assembly of SIV virus-like particles containing envelope proteins using a baculovirus expression system," Virology, 1995, 214:50-58.

Yao, "Enhancement of Mucosal Immune Responses by Chimeric Influenza HA/SHIV Virus-Like Particles," Res Initiat Treat Action, 2003, 8:20-21.

Zhao et al., "Boosting of SIV-specific immune responses in rhesus macaques by repeated administration of Ad5hr-SIVenv/rev and Ad5hr-SIVgag recombinants," Vaccine, 2003, 21:4022-4035.

Zhao et al., "Enhanced cellular immunity to SIV Gag following co-administration of adenoviruses encoding wild-type or mutant HIV Tat and SIV Gag," Virology, 2005, 342:1-12.

U.S. Appl. No. 16/996,740, dated Aug. 18, 2020, Michael A. Barry, Issued as U.S. Pat. No. 11,149,286.

U.S. Appl. No. 17/469,569, filed Sep. 8, 2021, Michael A. Barry, Published as U.S. 2022/0049271.

\* cited by examiner

α-Ad5 fiber tail

```
ATGAAGAGGGCTAGACCAAGCGAGGACACCTTCAATCCCGTCTACCCGTACG
ATACCGAGACCGGCCCTCCTACCGTGCCCTTCTTGACTCCCCCTTTCGTCTCC
CCTAACGGGTTTCAGGAATCTCCACCCGGGGTGCTGAGCCTGCGCCTGTCAG
AACCGCTGGTGACATCCAACGGCATGCTGGCCCTCAAGATGGGGAATGGCCT
GAGCCTCGACGAGGCCGGTAATCTCACGTCTCAGAACGTCACGACCGTGTCT
CCTCCGCTGAAGAAGACGAAGTCGAACATCAACCTGGAAATCAGCGCACCCC
TGACCGTGACAAGCGAGGCCCTTACTGTGGCAGCGGCAGCCCCCTCATGGT
GGCTGGCAATACCCTGACTATGCAGTCGCAGGCGCCCTGACAGTGCACGAC
TCTAAGCTGAGTATCGCGACCCAGGGACCTCTCACTGTCAGTGAGGGGAAGC
TAGCCCTGCAGACATCCGGCCCTCTGACAACAACCGACAGCTCAACTCTGACC
ATCACCGCCTCACCGCCGCTGACAACCGCTACCGGGTCCCTGGGCATCGACC
TAAAGGAGCCCATTTATACCCAGAACGGGAAGCTCGGCCTCAAGTACGGCGC
ACCGCTGCACGTGACCGACGACTTAAACACCCTGACCGTCGCCACCGGCCCA
GGCGTGACAATCAATAACACAAGTCTGCAGACGAAGGTAACCGGCGCCCTGG
GATTCGACAGCCAGGGCAATATGCAGCTCAACGTGGCCGGAGGGCTGCGCAT
TGACAGCCAGAATCGCAGGCTCATCCTCGACGTGAGCTACCCCTTCGACGCC
CAAAACCAGCTCAACCTCCGGCTGGGCCAGGGGCCGCTGTTCATTAATTCTG
CCCACAACCTGGACATCAACTATAACAAAGGCCTGTACCTGTTCACCGCCAGC
AACAACAGCAAAAACTGGAGGTGAACCTCTCCACGGCCAAGGGTCTCATGTT
TGACGCCACCGCAATCGCCATCAACGCAGGCGACGGCCTGGAGTTTGGCTCC
CCCAACGCCCCAAACACCAATCCACTGAAGACTAAGATTGGGCACGGCCTCG
AGTTCGACTCCAATAAGGCGATGGTGCCAAAGCTGGGCACGGGCCTCAGTTT
CGACTCCACTGGTGCTATCACCGTGGGAAACAAAACAACGACAAGCTGACCC
TGTGGACCACCCCGCCCCAGCCCCAACTGCCGCTTGAACGCCGAGAAGGA
CGCGAAACTGACCCTCGTGCTTACTAAGTGTGGAAGTCAAATCCTTGCTACGG
TCAGCGTTCTGGCGGTCAAGGGCTCGCTCGCCCCATCAGCGGGACGGTCCA
GTCCGCCCACCTCATCATCCGGTTCGACGAAACGGAGTGCTTCTGAACAACT
CCTTCCTGGACCCCGAGTACTGGAACTTCCGTAACGGCGACCTAACCGAGGG
TACCGCGTATACCAACGCCGTGGGATTTATGCCCAACCTGTCGGCTTACCCCA
AGTCTCATGGCAAGACTGCCAAGTCCAACATCGTTTCGCAGGTGTACTTGAAC
GGCGATAAGACCAAGCCCGTGACGTTGACGATTACCCTGAACGGTACCCAGG
AGACCGGCGACACCACCGAACAGAAGCTGATCTCTGAGGAGGACCTGGGCG
GGAGCTCGGGCACTAGTTACCCATATGACGTTCCAGACTACGCAGGCGGTTC
CCCCTCCGCCTATAGCATGTCTTTCAGCTGGGATTGGAGCGGGCACAACTACA
TAAACGAAATCTTCGCTACCTCCTCCTACACCTTCTCCTACATTGCCCAGTCTA
GAGAATAA
```

FIG. 6

SINGLE CYCLE REPLICATING ADENOVIRUS VECTORS

CROSS-REFERENCE TO RELATED APPLICATIONS

This application is a continuation of U.S. application Ser. No. 16/863,705, filed Apr. 30, 2020 (now U.S. Pat. No. 11,279,953), which is a continuation of U.S. application Ser. No. 16/570,535, filed Sep. 13, 2019 (now U.S. Pat. No. 10,640,786), which is a continuation of U.S. application Ser. No. 16/153,880, filed Oct. 8, 2018 (now U.S. Pat. No. 10,465,206), which is a divisional of U.S. application Ser. No. 12/920,775, filed Sep. 2, 2010 (now U.S. Pat. No. 10,131,921), which is a National Stage application under 35 U.S.C. § 371 of International Application No. PCT/US2009/036392, filed Mar. 6, 2009, which claims priority from U.S. Provisional Application Ser. No. 61/068,287, filed Mar. 6, 2008. The disclosures of the prior applications are considered part of (and are incorporated by referenced in) the disclosure of this application.

TECHNICAL FIELD

This document relates to adenovirus vectors and methods and materials related to using adenovirus vectors.

BACKGROUND INFORMATION

Adenoviruses can be easy to grow and manipulate, and they can exhibit broad host range in vitro and in vivo. The adenovirus life cycle does not require integration into the host cell genome, and foreign genes can be delivered using adenovirus vectors. For example, adenovirus vectors were successfully used in eukaryotic gene expression and vaccine development (Casimiro et al., J. Virol., 77:6305-6313 (2003); Benson et al., J. Virol., 72:4170-4182 (1998); Buge et al., J. Virol., 73:7430-7440 (1999); and Robert-Guroff et al., J. Virol., 72:10275-10280 (1998)).

SUMMARY

This document relates to adenovirus vectors and methods and materials related to using adenovirus vectors. For example, this document provides viruses, nucleic acid molecules encoding viruses, cell lines containing viral vectors, and methods for using viruses to deliver nucleic acid to cells in vitro or in vivo. This document also provides methods for using adenovirus vectors to induce immune responses and to treat cancer patients. In some cases, single cycle replicating adenoviruses can be used to deliver antigens that trigger an immune response within a mammal.

The nucleic acid molecules and viruses provided herein can lack all or a portion of the sequence encoding an adenovirus fiber protein and/or an adenovirus V protein and can contain a nucleic acid sequence that encodes one or more polypeptides that are heterologous to naturally occurring adenoviruses.

This document is based, in part, on the discovery that adenoviruses can be modified to create single cycle replicating adenoviruses. This document also is based, in part, on the discovery that single cycle replicating adenoviruses can be used to deliver nucleic acid encoding antigens such that a mammal produces an effective immune response against those antigens.

In general, one aspect of this document features a method for inducing an immune response against an antigen in a mammal. The method comprises, or consists essentially of, administering an adenovirus to the mammal under conditions wherein the adenovirus infects a cell of the mammal, wherein the adenovirus comprises an adenovirus polypeptide and lacks at least a portion of a nucleic acid sequence that encodes the adenovirus polypeptide, wherein the adenovirus comprises a nucleic acid sequence encoding the antigen, and wherein expression of the antigen in the cell leads to induction of the immune response. The mammal can be a human. The antigen can be a tumor antigen. The tumor antigen can be NY-ESO, EBV-LMP, or a papilloma virus antigen. The cell can be an epithelial cell, a tumor cell, a hematopoietic cell, or an antigen presenting cell. The adenovirus polypeptide can be a fiber protein, a V protein, hexon, penton-base, or pIII.

In another aspect, this document features a method for delivering a therapeutic polypeptide to a mammal. The method comprises, or consists essentially of, administering an adenovirus to the mammal under conditions wherein the adenovirus infects a cell of the mammal, wherein the adenovirus comprises an adenovirus polypeptide and lacks at least a portion of a nucleic acid sequence that encodes the adenovirus polypeptide, wherein the adenovirus comprises a nucleic acid sequence encoding the therapeutic polypeptide. The mammal can be a human. The therapeutic polypeptide can be a thymidine kinase, a fusogenic glycoprotein, a tumor suppressor p53, a heat shock protein polypeptide. The cell can be a tumor cell, a hematopoietic cell, a liver cell, or a gastrointestinal cell. The adenovirus polypeptide can be a fiber protein, a V protein, hexon, penton-base, or pIII.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 6 is a sequence listing for a nucleic acid sequence (SEQ ID NO:1) encoding a codon-optimized fiber protein.

DETAILED DESCRIPTION

Figure 1A:
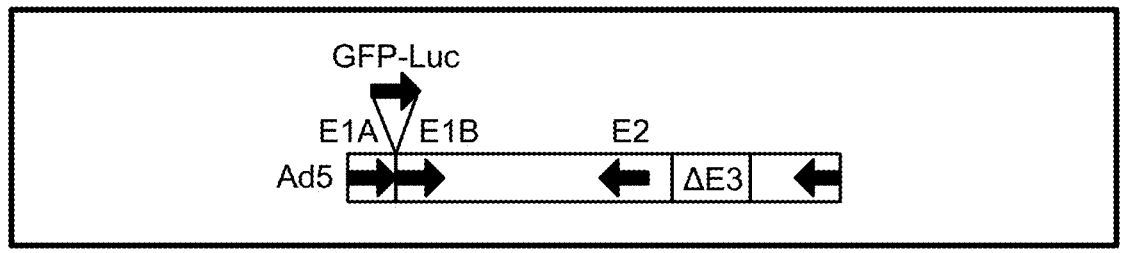
FIG. 1A is a schematic diagram of the Ad-rep-GFP-Luc vector.

This document provides viruses (e.g., single cycle replicating adenoviruses), nucleic acid molecules encoding viruses, cell lines containing viral vectors, methods for using viruses to deliver nucleic acid to cells in vitro or in vivo, methods for using adenovirus vectors to induce immune responses, and methods for using adenovirus vectors to treat cancer patients.

This document provides nucleic acid molecules that can encode single cycle replicating adenoviruses. Nucleic acid molecules encoding single cycle replicating adenoviruses can include all the naturally-occurring sequences of an adenovirus (e.g., an Ad5 virus) with the exception that it lacks all or a portion of at least one of the following adenovirus sequences: fiber protein-encoding sequence, V protein-encoding sequence, hexon-encoding sequence, penton base-encoding sequence, VA RNA-encoding sequence, pIII protein-encoding sequence, or other early or late gene product-encoding sequences. Examples of adenoviral nucleic acid sequences that encode polypeptides include, without limitation, those set forth in GenBank gi numbers 209842, 58478, or 2935210, and/or annotated in GenBank accession numbers M73260, X17016, or AF030154.

In some cases, a deletion of all or a portion of the nucleic acid encoding one or more of the following polypeptides can be engineered into a nucleic acid encoding an adenovirus: fiber protein-encoding sequence, V protein-encoding sequence, hexon-encoding sequence, penton base-encoding sequence, VA RNA-encoding sequence, pIII protein-encoding sequence, or other early or late gene product-encoding sequences. Such deletions can be any length that results in the deletion of one or more encoded amino acids. For example, portions of a nucleic acid sequence of an adenovirus can be removed such that an encoded polypeptide lacks 5, 6, 7, 8, 9, 10, 15, 20, 25, 30, or more amino acid residues). The portion or portions to be deleted can be removed from any location along the length of the sequence. For example, a portion of an adenovirus nucleic acid sequence can be removed at the 5' end, the 3' end, or an internal region of an adenovirus nucleic acid such as a fiber protein-encoding sequence, V protein-encoding sequence, hexon-encoding sequence, penton base-encoding sequence, VA RNA-encoding sequence, pIII protein-encoding sequence, or other early or late gene product-encoding sequences.

Any appropriate molecular biology and biochemical method (e.g., nucleic acid sequencing) can be used to identify the presence and location of a deletion introduced into an adenovirus nucleic acid. For example, nucleic acids can be separated by size using gel electrophoresis to confirm that portions have been removed relative to the length of the original nucleic acid. In some cases, antibodies that recognize various epitopes on the encoded polypeptide (e.g., a fiber polypeptide) can be used to detect the presence or absence polypeptides targeted for deletion.

In some cases, a nucleic acid molecule provided herein can include a sequence encoding a therapeutic polypeptide or an immunogen. Examples of therapeutic polypeptides include, without limitation, propionyl CoA carboxylase (NM 000282; gi number 5095), dystrophin (M92650; gi number 1756), p53 (M14695), factor IX (BC109215; gi number 7157), herpes virus thymidine kinase (NC 001798), measles H and F fusogenic glycoproteins (DQ227321; gi number 1489803), sodium iodide symporter (NM_000453; gi number 6528), and heat shock protein (L12723; gi number 3308). Expression of such therapeutic polypeptides can be driven by, for example, linking polypeptide encoding sequences to constitutive, inducible, and/or tissue-specific promoter sequences that can drive transcription of a therapeutic polypeptide. Examples of immunogens include, without limitation, cancer immunogens such as melanoma antigen family A (NM_004988; gi number 4100), MUC1 (Z17325; gi number 4582), Epstein-Barr virus LMP-2 (V01555), and human papilloma virus proteins (K02718), viral immunogens such as HIV gag and env (NC 001802), influenza hemagglutinin (EU497921), hepatitis C core (NC 004102; gi number 951475), and smallpox H3L antigen (DQ437592), and bacterial immunogens such as *Bacillis anthracis* protective antigen (AF268967) and mecA from *Staphylococcus aureus* (AB353125). In some cases, an immunogen can be a full-length immunogenic polypeptide or a portion thereof. For example, a nucleic acid sequence encoding an immunogenic polypeptide can be modified to remove portions of nucleic acid such that the encoded polypeptide lacks any number of amino acids (e.g., 5, 10, 15, 20, 30 amino acids, or all amino acids of the immunogenic polypeptide). In some cases, portions of a nucleic acid sequence encoding an immunogenic polypeptide can be removed from anywhere along the length of the sequence. For example, portions of the nucleic acid sequence can be removed at the 5' end, the 3' end, or an internal region of the target nucleic acid. In some cases, a therapeutic polypeptide and/or an immunogenic polypeptide can be designed to be secreted from cells infected with the adenovirus encoding the therapeutic polypeptide and/or immunogenic polypeptide.

Any appropriate method can be used to detect expression of a therapeutic polypeptide or immunogenic polypeptide from virus infected cells. For example, antibodies that recognize a therapeutic polypeptide or immunogenic polypeptide can be used to detect the presence or absence of the polypeptide in infected cells.

The term "nucleic acid" as used herein encompasses both RNA and DNA, including cDNA, genomic DNA, and synthetic (e.g., chemically synthesized) DNA. A nucleic acid can be double-stranded or single-stranded. A single-stranded nucleic acid can be the sense strand or the antisense strand. In addition, a nucleic acid can be circular or linear.

An "isolated nucleic acid" refers to a nucleic acid that is separated from other nucleic acid molecules that are present in a viral genome, including nucleic acids that normally flank one or both sides of the nucleic acid in a viral genome. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., any paramyxovirus, retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

As described herein, a nucleic acid molecule can encode an adenovirus with the exception that it lacks all or a portion of at least of one adenovirus polypeptide-encoding sequence. Any appropriate molecular cloning technique (e.g., recombination or site-directed mutagenesis) can be used to generate an adenovirus nucleic acid molecule that lacks all or a portion of a fiber protein-encoding sequence, a V protein-encoding sequence, hexon protein-encoding sequence, penton base protein-encoding sequence, VA RNA-encoding sequence, or pIII protein-encoding sequence. Likewise, any appropriate molecular cloning technique (e.g., PCR, recombination, or restriction site cloning) can be used to introduce a nucleic acid sequence into a nucleic acid molecule of an adenovirus. The nucleic acid molecules provided herein can be incorporated into viruses by standard techniques. For example, recombinant techniques can be used to insert a nucleic acid molecule provided herein into an infective viral genome or sub-genome within a plasmid or other vector. In some cases, a plasmid or other vector can additionally express luciferase or another reporter gene. The viral genome can then be transfected into mammalian cells to rescue the modified adenovirus. Alternately, modified subgenome sequences can be co-transfected into cells with other subgenome sequence such that the mammalian cells recombines the subgenomes into an intact genome making new virus.

The document also provides viruses (e.g., adenoviruses) containing a nucleic acid molecule provided herein. For example, this document provides recombinant adenoviruses that lack all or a portion of a fiber protein-encoding sequence, a V protein-encoding sequence, a hexon protein-encoding sequence, a penton base protein-encoding sequence, a VA RNA-encoding sequence, a pIII protein-encoding sequence, or other early or late gene product-encoding sequence. In some cases, such adenoviruses can contain the polypeptide while lacking all or a portion of the nucleic acid sequence that encodes that polypeptide. For example, an adenovirus provided herein can be contain adenovirus fiber protein while lacking the nucleic acid that encodes adenovirus fiber protein. Such adenoviruses can be obtained using cells lines designed to express the polypeptide such that it is incorporated into virus particles that lack the nucleic acid sequence that encodes that polypeptide.

This document provides cell lines that can be used to produce viruses (e.g., adenoviruses) that contain a particular polypeptide while lacking the nucleic acid sequence that encodes that polypeptide. For example, this document provides isolated cells that express an adenovirus fiber protein, an adenovirus V protein, an adenovirus hexon protein, an adenovirus penton base protein, an adenovirus VA RNA, an adenovirus pIII protein, or other adenovirus early or late gene product. Such cells can contain nucleic acid that allows adenovirus particles to be produced such that they contain the expressed adenovirus polypeptide, while lacking the nucleic acid sequence that encodes that polypeptide.

The viruses provided herein can be used to induce immune responses within a mammal and/or can be used to treat cancer. For example, an adenovirus can be designed to be a single cycle replicating adenovirus (e.g., a fiber protein-less or V protein-less adenovirus) that contains nucleic acid that drives expression of a cancer immunogen. Such an adenovirus can be propagated in a cell that provides the missing adenovirus polypeptide (e.g., fiber protein-expressing cell line or V protein-expressing cell line) in order to increase the available number of copies of that virus, typically by at least 100-fold (e.g., by 100-fold to 15,000-fold, by 500- to 10,000-fold, by 5,000- to 10,000-fold, or by 5,000- to 15,000-fold). A virus can be expanded until a desired concentration is obtained in standard cell culture media (e.g., DMEM or RPMI-1640 supplemented with 5-10% fetal bovine serum at 37° C. in 5% $CO_2$). A viral titer typically is assayed by inoculating cells (e.g., A549 or 293 cells) in culture or by quantitating viral genomes by optical density or real-time PCR.

Viral stocks can be produced by growth in mammalian cells. Viral stocks can be aliquoted and frozen, and can be stored at −70° C. to −80° C. at concentrations higher than the therapeutically effective dose. A viral stock can be stored in a stabilizing solution. Examples of stabilizing solutions include, without limitation, sugars (e.g., trehalose, dextrose, glucose), amino acids, glycerol, gelatin, monosodium glutamate, $Ca^{2+}$, and $Mg^{2+}$.

The viruses provided herein can be administered to a mammal to deliver an encoded therapeutic polypeptide or to induce an immune response against an encoded immunogen. For example, a composition containing a virus provided herein can be administered to a mammal by, for example, subcutaneous, intramuscular, intravenous, intratumoral, or oral administration. In some cases, the viruses provided herein can be designed to induce an anti-cancer immune response. Examples of types of cancers that can be treated using the viruses provided herein include, without limitation, myeloma, melanoma, glioma, lymphoma, leukemia, and cancers of the lung, brain, stomach, colon, rectum, kidney, prostate, ovary, and breast. For example, an adenovirus lacking fiber protein-encoding nucleic acid and containing a gp100 or fusogenic glycoprotein polypeptide fragment can be used to treat melanoma.

The viruses provided herein can be administered to a mammal (e.g., a human) in a biologically compatible solution or a pharmaceutically acceptable delivery vehicle. Suitable pharmaceutical formulations depend in part upon the use and the route of entry, e.g., transdermal or by injection. Such forms should not prevent the composition or formulation from reaching target cells (e.g., immune cells, or tumor cells) or from exerting its effect. For example, pharmacological compositions injected into the blood stream should be soluble.

While dosages administered can vary from patient to patient (e.g., depending upon desired response or the disease state), an effective dose can be determined by setting as a lower limit the concentration of virus proven to be safe and escalating to higher doses, while monitoring for the desired response (e.g., antibody production, T cell responses, a reduction in cancer cell growth, or reduction in cancer-associated protein) along with the presence of any deleterious side effects.

The viruses provided herein can be delivered in a dose ranging from, for example, about $10^3$ pfu to about $10^{12}$ pfu (typically >$10^8$ pfu). A therapeutically effective dose can be provided in repeated doses. Repeat dosing is appropriate in cases in which observations of clinical symptoms or tumor size or monitoring assays indicate either that a group of cancer cells or tumor has stopped shrinking or that the degree of viral activity is declining while the tumor is still present. Repeat doses (using the same or a different modified virus) can be administered by the same route as initially used or by another route. A therapeutically effective dose can be delivered in several discrete doses (e.g., days or weeks apart) and in some cases, one to about twelve doses are provided. In some cases, a therapeutically effective dose of viruses can be delivered by a sustained release formulation.

The invention will be further described in the following examples, which do not limit the scope of the invention described in the claims.

EXAMPLES

Figure 1B:
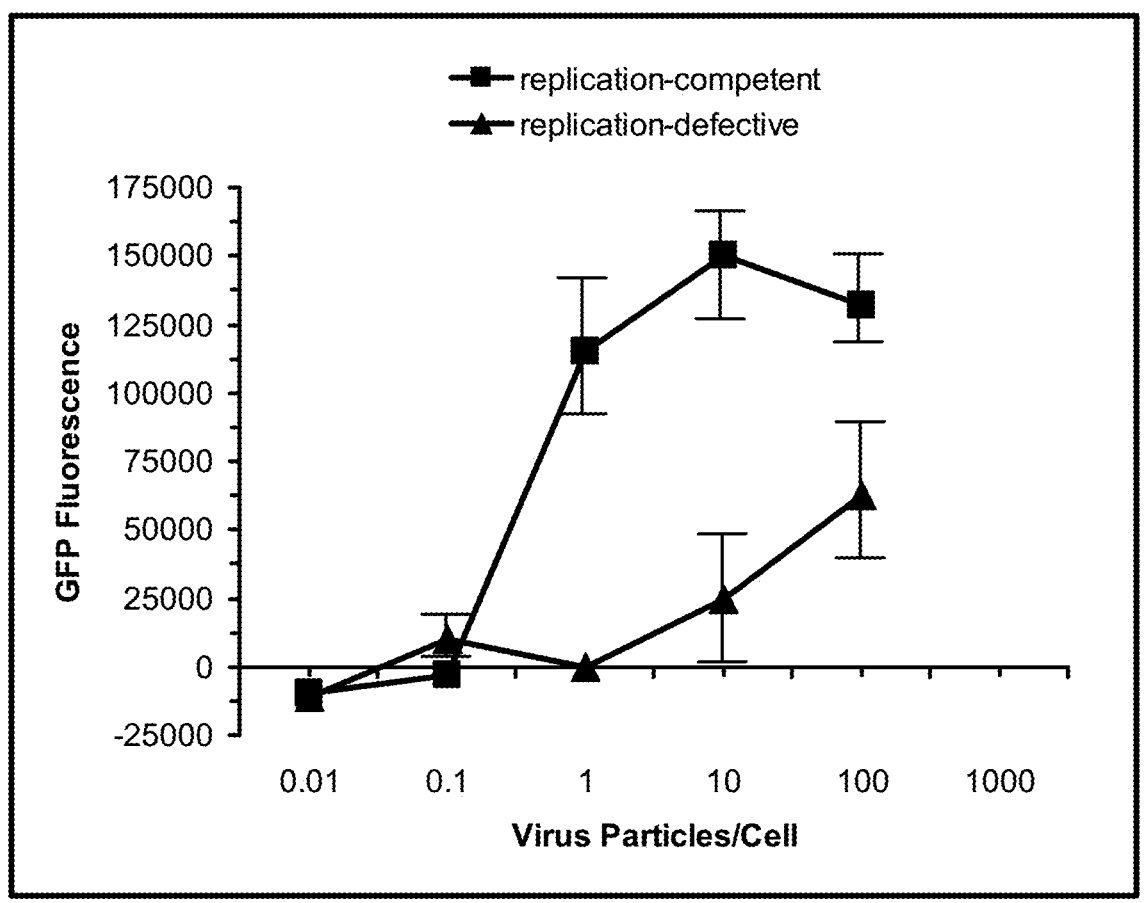
FIG. 1B is a graph plotting GFP expression after infection with the indicated virus particle/cell ratios on a microplate reader.

Example 1—Comparing Replication-Competent Vs. Replication-Defective Adenoviruses To determine whether replicating adenovirus vectors generate better immune responses than replication-defective adenovirus vectors after oral delivery, replication-competent Ad5 was modified to over-express transgenes by inserting a CMV-GFP-luciferase expression cassette at a HpaI site between E1a and E1b (FIG. 1A). In vitro comparison of GFP fluorescence between replication-competent (Ad-rep-GFP-Luc) and replication-defective Ad in vitro demonstrated that the replication-competent vector expressed transgenes to a much higher level at equal virus particles/cell (FIG. 1B).

Figure 2A:
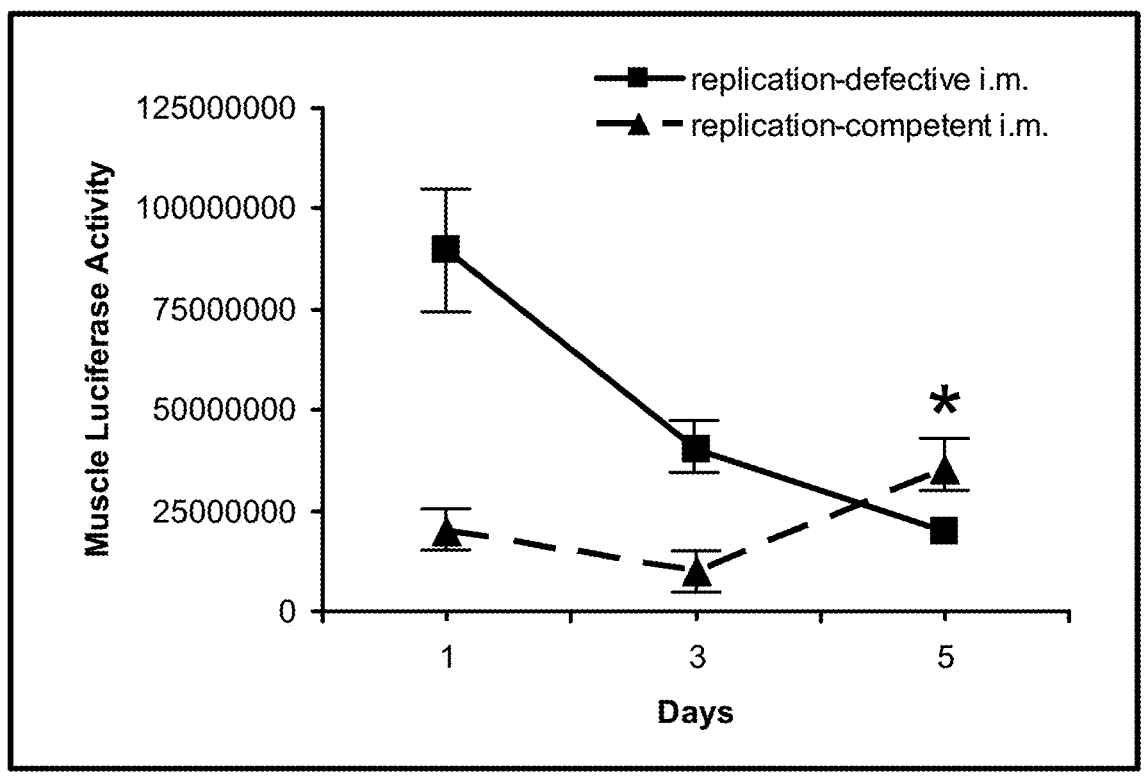
FIG. 2A is a graph plotting muscle luciferase activity in mice infected with replication-defective or replication-competent Ad5 vectors on the indicated day post infection. $1 \times 10^{10}$ virus particles of the indicated GFP-Luc expressing viruses were administered intramuscularly into mice. The mice were imaged on a Lumazone for luciferase activity on the indicated days. The results are shown for the mean photons for the injection site indicating expression of the luciferase transgene in the tissues. * indicates p value of 0.0276 for last time point.
Figure 2B:
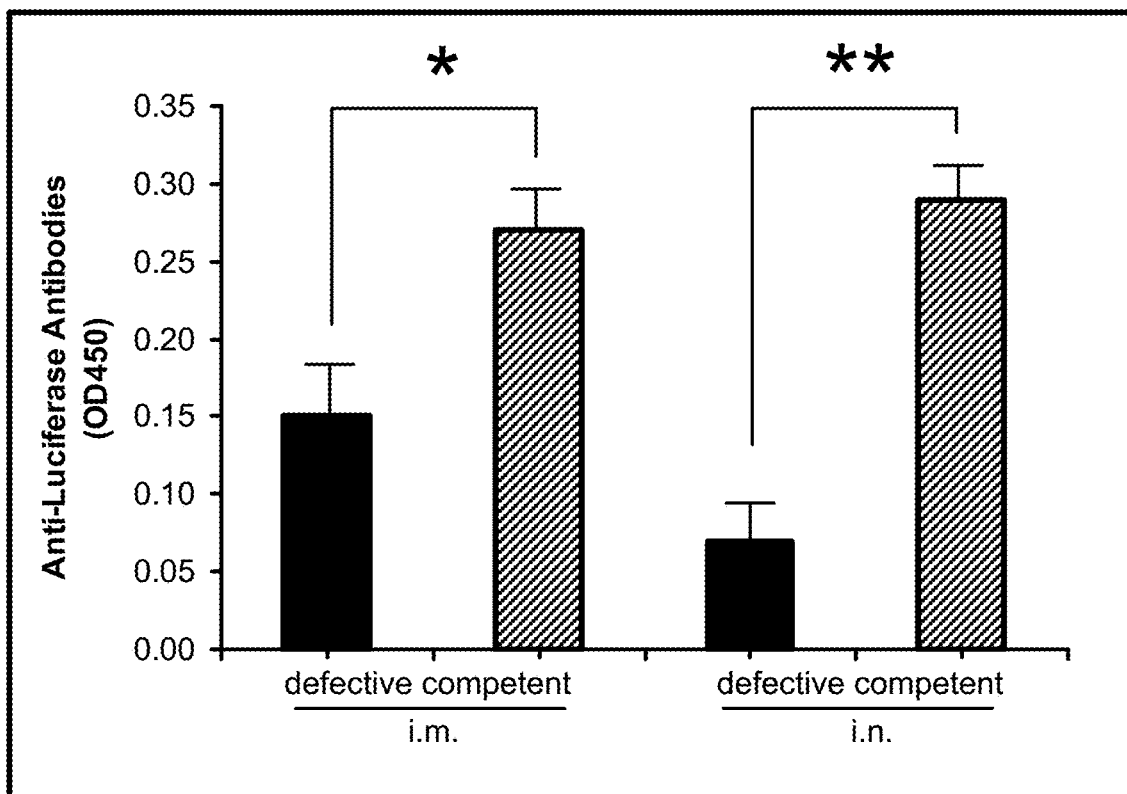
FIG. 2B is a bar graph plotting anti-luciferase antibody responses for BALB/c mice immunized intramuscularly (i.m.) or intranasally (i.n.) with the indicated vectors. The antibody responses against luciferase were measured from serum 3 weeks later. Significance was 0.0026 by one way ANOVA. * and ** indicate p values of 0.038 and 0.0008, respectively, by Bonferroni's multiple comparison test.

When the Ad-rep-GFP-Luc replication-competent vector was tested in vivo in nude mice bearing human tumors, luciferase imaging revealed the virus first seeds the liver, replicates, and then expands into tumors (FIG. 1C). Direct comparison of luciferase activity after intramuscular injection demonstrated that the replication-competent vector produced less luciferase initially, but that transgene expression appeared to increase over time in contrast to the replication-defective virus (FIG. 2A). This increase was not observed after intranasal administration. Imaging captures only the strongest localized signals, however, and dispersed lower expression may not be captured. When immune responses were compared, it was demonstrated that the replication-competent vectors generated substantially higher immune responses against the transgene products by both routes (FIG. 2B), indicating that the viruses replicate sufficiently in the mouse model to evaluate their utility as vaccine carriers.

These results demonstrate that replicating adenovirus vectors such as Ad-rep-GFP-Luc can be used as delivery vectors. These results also demonstrate that replicating adenovirus vectors can be used to induce effective immune responses in mammals.

Figure 3A:
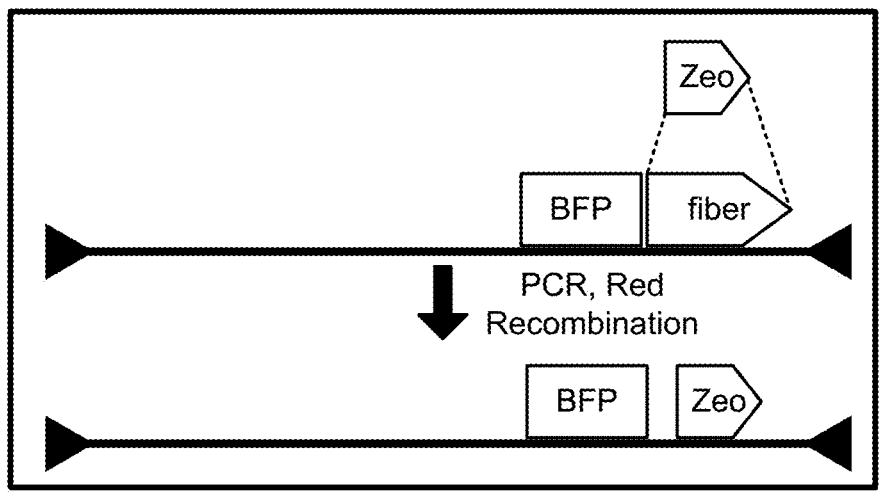
FIG. 3A contains a schematic diagram of a Ad-Blue-ΔF vector. Expression of the Ad-Blue-ΔF vector was detected by fluorescent imaging of BFP in transfected cells.

Example 2—Single Cycle Replicating Adenoviruses Based on Deletion of the Late Gene for the Fiber Protein The adenovirus fiber protein mediates binding to its receptor CAR (Campos and Barry, *Curr. Gene Ther.*, 7:189-204 (2007)). Viruses lacking fiber are defective due to loss of CAR binding and due to incomplete maturation of virus particles. The viral genome plasmid Ad-Blue-ΔF was constructed in which the entire fiber coding sequence was replaced with a zeocin-resistance marker by recombination in bacteria (FIG. 3A). This virus carried the blue fluorescent protein (BFP) gene in the E3 region that is expressed only in replicating virions to mark successful replication of the vector. When this fiber-deleted genome was transfected into 293 cells, western blot analysis demonstrated that this vector expresses no fiber proteins. When this virus was propagated in 293 cells, it failed to spread to other cells (FIG. 3A). In contrast, when the same genome was transfected into fiber-expressing 633 cells, virus production was rescued. Therefore, a single-cycle Ad vector can be produced in fiber-expressing 633 cells, but they cannot spread after initial infection because they lack the fiber gene. By growing Ad-Blue-ΔF in 633 cells, normal yields of virions displaying fibers were produced, but they did not contain nucleic acid encoding fibers. By growing Ad-Blue-ΔF in 633 cells and then 293 cells in the last round of amplification, Ad-Blue-ΔF without fiber were produced in normal yields (e.g. $5 \times 10^{12}$ virus particle preps). Therefore, this system can be used to make large batches of Ad vaccines displaying fiber proteins, but that cannot produce new virions with fibers after infection in vivo.

Figure 3B:
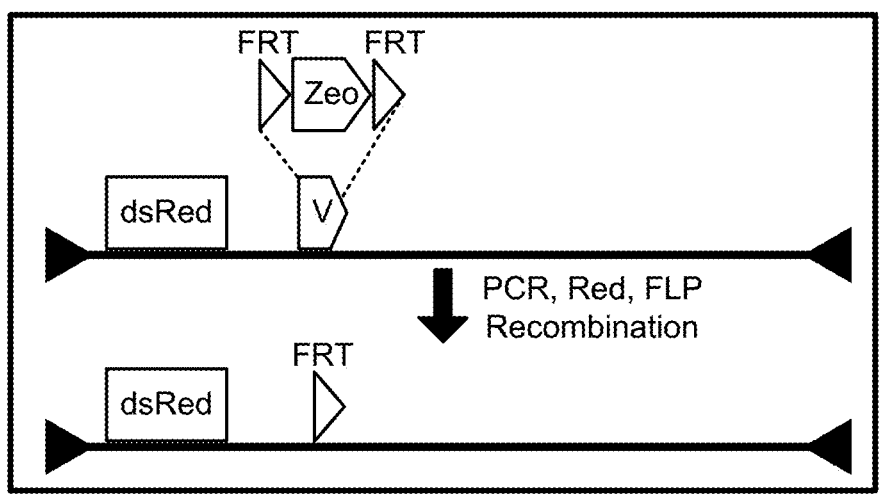
FIG. 3B contains a schematic diagram of a Ad-Red-ΔV vector and photographs of cells transfected with the viral genomes at 2 and 21 days. dsRed expression was detected in cells transfected with each vector by the detection of red fluorescence. Brightfield images demonstrated that the deleted-fiber vector grows efficiently when fiber is supplied from the cell line. Unlike wild-type virus with intact protein V, the ΔV vector does not form red plaques after 3 weeks indicating that the deletion has rendered the virus defective for virus production and spread.

Example 3—Single Cycle Replicating Adenoviruses Based on Deletion of the Early Gene for Protein V Protein V is a 42 kDa protein present at 160 copies per Ad virion (Campos and Barry, *Curr. Gene Ther.*, 7:189-204 (2007)). The following was performed to test whether protein V can be deleted from Ad5 by knocking the gene out in a dsRed-expressing vector by homologous recombination in bacteria (FIG. 3B). When tested in 293 cells, Ad-Red-ΔV produced reporter gene product, but never plaqued (FIG. 3B). These results demonstrate that viruses containing a deleted protein V can be used to generate single-cycle replicating viruses. In this case, deletion of protein V targets an early gene product rather than the late fiber gene. ΔV viruses produced in cell lines expressing protein V in trans (like fiber-expressing 633 cells) can encapsidate protein V, allowing progeny virions to infect and transduce cells in vivo. Following infection as a vaccine in vivo, viral ΔV genomes can be replicated normally. However, progeny virions would lack protein V and would be unable to infect actively a second set of cells after the initial infection.

In summary, these results demonstrate that, unlike a replication-competent Ad, single-cycle fiberless or protein V deleted Ad progeny virions can be infectious only when administered. Secondary virions cannot propagate an uncontrolled adenovirus infection like live Ad4, 5, and 7 vaccines and cannot be spread or cause disease in people in close or distant contact with the vaccine or person receiving the therapeutic. Unlike replication-defective Ad vaccines, fiber-deleted Ad produced from 633 cells or protein V-deleted virions can replicate their genomes and antigen genes 10,000-fold in infected cells. These single-cycle viruses therefore can be used to amplify antigen production without the risk of causing uncontrolled adenovirus infections.

Example 4—Codon-Optimized Fiber Expression

Figure 4:
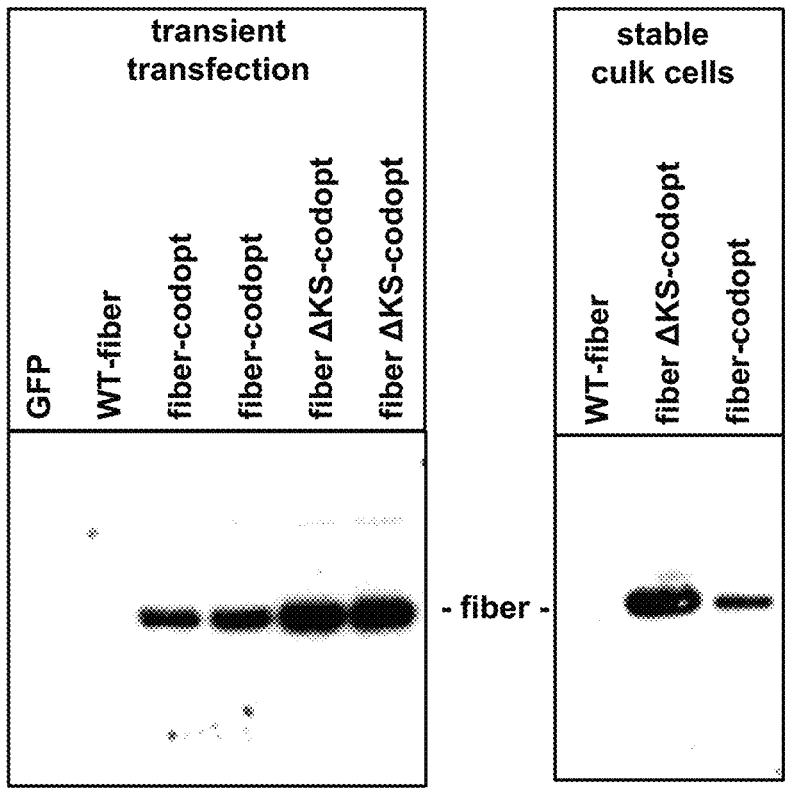
FIG. 4 contains Western blot results of wild-type and codon-optimized fiber expression in the indicated cells for use as helper cells to produce fiber-deleted viruses.
Figure 4:
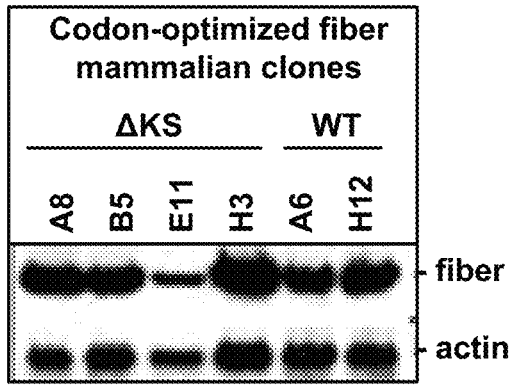

Western blot analysis was performed to test the use of codon-optimized fiber expression in various cell lines for use as helper cells to produce fiber-deleted viruses. The nucleic acid sequence encoding a codon-optimized fiber protein used for the expression assays was as set forth in SEQ ID NO:1. As demonstrated in FIG. 4, transiently- and stably-transfected cells can produce fiber-deleted viruses. Fluorescent imaging of transfected 293 cells revealed robust plaque formation of BFP-expressing Ad with fiber-deletion in 293 cells stably expressing codon-optimized fiber, but poor plaque formation in 293 cells lacking fiber. These results demonstrate that cells expressing codon-optimized fiber can be used to propagate viruses with fiber-deletion genomes. These results also demonstrate that cells expressing codon-optimized fiber can be used to establish fiber libraries.

Figure 5:
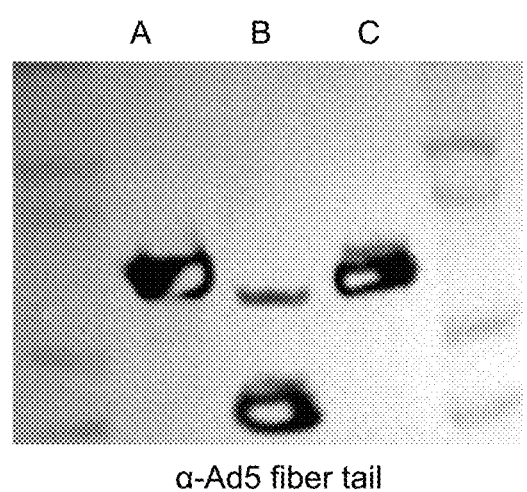
FIG. 5 contains Western blot results of cesium chloride (CsCl) purified wild-type Ad5 vector (A) and Ad5 with fiber deletion (C) expressed in transfected 293 cells. An irrevernt Ad5 modified with short and long fibers from Ad41 is also shown (B). Western blotting was performed using an antibody that recognizes the N-termini of the fiber proteins.

To assess fiber protein incorporation into Ad viruses with a fiber-deletion genome, western blot analysis was performed on viruses produced by infection of 293 cells with Ad5 vector (FIG. 5A), by infection of codon-optimized fiber-expressing 293 cells with Ad5 with fiber-deletion (FIG. 5C), or by infection of 293 cells with an irreverent Ad5 modified with short and long fibers from Ad41 (FIG. 5B). Viruses were purified by banding in a cesium chloride (CsCl) gradient. Western blots were performed using an antibody that recognized the N-terminus of the fiber protein. Western blot data revealed that when the fiber-deleted Ad5 virus was propagated in codon-optimized fiber-expressing 293 cells, the cells produced sufficient levels of fiber protein for normal fiber incorporation into Ad virions (FIG. 5).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for inducing an immune response against an antigen in a mammal, wherein said method comprises:
    (a) providing an initial administration of a single cycle replicating adenovirus to said mammal under conditions wherein said adenovirus infects a cell of said mammal and replicates within said cell, wherein said cell does not produce new infectious virions following infection with said adenovirus, wherein said adenovirus comprises an adenovirus polypeptide and lacks at least a portion of a nucleic acid sequence that encodes said adenovirus polypeptide, wherein when said adenovirus lacks at least a portion of a nucleic acid sequence that encodes a fiber protein, said adenovirus comprises a fiber protein having wild-type specificity, wherein said adenovirus comprises a nucleic acid sequence encoding said antigen, and wherein expression of said antigen in said cell leads to induction of said immune response, and
    (b) providing a repeated administration of said single cycle replicating adenovirus to said mammal.

2. The method of claim 1, wherein said mammal is a human.

3. The method of claim 1, wherein said antigen is a tumor antigen.

4. The method of claim 3, wherein said tumor antigen is NY-ESO, EBV-LMP, or a papilloma virus antigen.

5. The method of claim 1, wherein said cell is an epithelial cell, a tumor cell, a hematopoietic cell, or an antigen presenting cell.

6. The method of claim 1, wherein said adenovirus polypeptide is a fiber protein, a V protein, hexon, penton-base, or pIII.

* * * * *

SEQUENCE LISTING

```
<160> NUMBER OF SEQ ID NOS: 1

<210> SEQ ID NO 1
<211> LENGTH: 1839
<212> TYPE: DNA
<213> ORGANISM: Artificial Sequence
<220> FEATURE:
<223> OTHER INFORMATION: Nucleic acid encoding an adenovirus fiber
      protein

<400> SEQUENCE: 1
atgaagaggg ctagaccaag cgaggacacc ttcaatcccg tctaccgta cgataccgag      60 accggccctc ctaccgtgcc cttcttgact cccccttcg tctcccctaa cgggtttcag     120
gaatctccac ccggggtgct gagcctgcgc ctgtcagaac cgctggtgac atccaacggc    180
atgctggccc tcaagatggg gaatggcctg agcctcgacg aggccggtaa tctcacgtct    240
cagaacgtca cgaccgtgtc tcctccgctg aagaagacga agtcgaacat caacctggaa    300
atcagcgcac ccctgaccgt gacaagcgag gcccttactg tggcagcggc agcccccctc    360
atggtggctg gcaatacccc gactatgcag tcgcaggcgc cctgacagt gcacgactct    420 aagctgagta tcgcgaccca gggacctctc actgtcagtg aggggaagct agccctgcag    480
acatccggcc ctctgacaac aaccgacagc tcaactctga ccatcaccgc ctcaccgccg    540
ctgacaaccg ctaccgggtc cctgggcatc gacctaaagg agcccattta tacccagaac    600
gggaagctcg gcctcaagta cggcgcaccg ctgcacgtga ccgacgactt aaacaccctg    660
accgtcgcca ccggcccagg cgtgacaatc aataacacaa gtctgcagac gaaggtaacc    720
ggcgccctgg gattcgacag ccagggcaat atgcagctca acgtggccgg agggctgcgc    780 attgacagc agaatcgcag gctcatcctc gacgtgagct accccttcga cgcccaaaac    840
cagctcaacc tccggctggg ccagggggccg ctgttcatta attctgccca caacctggac    900
atcaactata acaaaggcct gtacctgttc accgccagca caacagcaa aaaactggag    960 gtgaacctct ccacggccaa gggtctcatg tttgacgcca ccgcaatcgc catcaacgca   1020
```

-continued

```
ggcgacggcc tggagtttgg ctcccccaac gccccaaaca ccaatccact gaagactaag    1080
attgggcacg gcctcgagtt cgactccaat aaggcgatgg tgccaaagct gggcacgggc    1140
ctcagtttcg actccactgg tgctatcacc gtgggaaaca aaaacaacga caagctgacc    1200
ctgtggacca cccccgcccc cagcccaac tgccgcttga acgccgagaa ggacgcgaaa     1260
ctgaccctcg tgcttactaa gtgtggaagt caaatccttg ctacggtcag cgttctggcg    1320
gtcaagggct cgctcgcccc catcagcggg acggtccagt ccgcccacct catcatccgg    1380
ttcgacgaaa acggagtgct tctgaacaac tccttcctgg accccgagta ctggaacttc    1440
cgtaaccgcg acctaaccga gggtaccgcg tataccaacg ccgtgggatt tatgcccaac    1500
ctgtcggctt accccaagtc tcatggcaag actgccaagt ccaacatcgt ttcgcaggtg    1560
tacttgaacg gcgataagac caagcccgtg acgttgacga ttaccctgaa cggtacccag    1620
gagaccggcg acaccaccga acagaagctg atctctgagg aggacctggg cgggagctcg    1680
ggcactagtt acccatatga cgttccagac tacgcaggcg gttcccctc cgcctatagc     1740 atgtctttca gctgggattg gagcgggcac aactacataa acgaaatctt cgctacctcc    1800
tcctacacct tctcctacat tgcccagtct agagaataa                            1839
```